United States Patent
Segal

(10) Patent No.: US 6,772,943 B2
(45) Date of Patent: Aug. 10, 2004

(54) SYSTEM AND METHOD FOR DOCUMENT STORAGE MANAGEMENT

(75) Inventor: Donald Segal, Silver Spring, MD (US)

(73) Assignee: Softmed Systems, Inc., Silver Spring, MD (US)

(*) Notice: Subject to any disclaimer, the term of this patent is extended or adjusted under 35 U.S.C. 154(b) by 27 days.

(21) Appl. No.: 10/079,815

(22) Filed: Feb. 22, 2002

(65) Prior Publication Data
US 2003/0160095 A1 Aug. 28, 2003

(51) Int. Cl.⁷ .............................................. G06F 17/00
(52) U.S. Cl. .............................. 235/375; 705/3; 705/8; 705/2
(58) Field of Search ................................ 235/375, 376, 235/383, 385; 705/2, 3, 8

(56) References Cited

U.S. PATENT DOCUMENTS

| 4,588,211 A | 5/1986 | Greene |
| 4,634,148 A | 1/1987 | Greene |
| 5,319,543 A * | 6/1994 | Wilhelm .......................... 705/3 |
| 5,684,288 A * | 11/1997 | Renvall ................. 235/462.15 |
| 5,772,585 A * | 6/1998 | Lavin et al. ................. 600/300 |
| 5,991,730 A * | 11/1999 | Lubin et al. .................... 705/3 |
| 6,088,695 A * | 7/2000 | Kara ............................ 707/10 |

* cited by examiner

Primary Examiner—Thien M. Le
Assistant Examiner—Daniel A. Hess
(74) Attorney, Agent, or Firm—Rothwell, Figg, Ernst & Manbeck, P.C.

(57) ABSTRACT

Documents to be scanned to create an electronic digital data record are printed with a machine-readable graphic code in which is embedded document-identifying information, such as the type of document and a characteristic identifying parameter with which the document is associated. Using the information provided in the graphic code, the scanned documents are automatically indexed according to document type and characteristic identifying parameter and are thereafter electronically stored in a memory area corresponding to the associated characteristic identifying parameter. When the document is first printed a record is made of the document so that when the documents are scanned, confirmation can be made that every document that is printed with a graphic code is subsequently scanned or otherwise accounted for. The electronically-stored documents can thereafter be easily and accurately accessed electronically.

27 Claims, 7 Drawing Sheets

ADDRESS-O-GRAPH — 210

ADMISSION AGREEMENT
FOR EMERGENCY ROOM, INPATIENT OR OUTPATIENT SERVICES

DAVIDSON, MARY    F
DR EMERGENCY-ROOM  056
00975              DEPT
0321945            OPER
000047628995       RMC

I. CONSENT FOR DIAGNOSIS AND TREATMENT

I am visiting/entering MEMORIAL HOSPITAL voluntarily for the purpose of diagnosis and medical or surgical treatment and consent to and authorize diagnostic procedures and medical, surgical, x-ray, nuclear, electrical and laboratory test or treatment and blood transfusions by my physician, his assistants or designees as are necessary in their judgment. I am aware that the practice of medicine and surgery is not an exact science and I acknowledge that no guarantees have been made to me as a result of treatment or examination in this hospital. I hereby authorize MEMORIAL HOSPITAL to retain, preserve and use or scientific or teaching purposes, or dispose of at their convenience any specimen or tissue taken from my body during my hospitalization.

II. RETENTION OF INFORMATION

I understand that MEMORIAL HOSPITAL may record medical and other information concerning my in electronic and other physical form. Such information is required in the course of my treatment, and may be released by the hospital for the purpose authorized on this form. I understand that portions of my records may be disclosed to qualified non-hospital personnel for the purpose of conducting scientific or statistical research, management or financial audits, licensure and program evaluation or other similar purpose. I will not be identified by name or other personally identifying information in any report of such research, audit or evaluation without my express consent.

III. RELEASE OF INFORMATION

I hereby authorize MEMORIAL HOSPITAL to release to my insurance companies, employer insurance groups, health plans, Medicaid/Medicare program, or any intermediaries, or physicians associated with the hospital and any billing or collection agents of MEMORIAL HOSPITAL, and medical or financial records or other information concerning this treatment to obtain reimbursement on my behalf for the treatment and services provided to me by MEMORIAL HOSPITAL and the physicians associated with the hospital. Further, I authorize MEMORIAL HOSPITAL to release any medical information concerning this treatment to physicians and clinicians associated with the hospital who are my healthcare providers. I may revoke my authorization and consent at any time for any reason by providing written notice to MEMORIAL HOSPITAL. This authorization shall not conflict with any internal policy regarding my treatment for services requiring a restricted release under State or Federal Law.

I HAVE READ each of the foregoing, I-III and fully agree to each of the statements and agreements herein, which may include inpatient treatment after emergency or outpatient, by signing below as my free and voluntary act.

VERBAL CONSENT  ☐ YES  ☐ NO

Patient Signature _____ Date _____

Parent or Guardian (patient under 18 years old) _____ Date _____

Other (relationship to patient) _____ Date _____

Insured (if other than patient) _____ Date _____

Witness _____

SYSTEM AND METHOD FOR DOCUMENT STORAGE MANAGEMENT

FIELD OF THE INVENTION

The present invention relates to a system and method for document creation, storage, indexing, and tracking. In particular, varying types of documents, each being uniquely associated with a particular characteristic identifying parameter, are created, stored, indexed, and tracked by a system and method which substantially reduces the time and manual labor required for filing, indexing, and retrieving documents and improves the accuracy of document filing by reducing the likelihood of misfiled or lost documents.

BACKGROUND OF THE INVENTION

In enterprises in which substantial amounts of documentation are generated on a regular basis, managing such documentation, for example storing, tracking, indexing, and later retrieving when/as needed, can be a significant burden on the enterprise in terms of labor and space requirements, costs, and the possibility of documents being lost or misfiled. This burden can be particularly acute, for example, in the management of patient charts at a hospital. A patient chart is created for each patient admitted into the hospital, and, for even short hospital visits, numerous forms, e.g., admission forms, consent forms, payment forms, progress notes, etc., are prepared and completed during the visit. All of the forms must be tracked and filed in the appropriate patient chart.

A typical hospital admission form 220 is shown in FIG. 3. This is a fairly standard form, and for any given hospital or related network of hospitals, the form will be identical for all patients for which such a form is applicable. In the upper right-hand corner of the form is a blank space 210 at which document identifying information is provided. In systems presently at use in many hospitals, such blank forms are stored in forms bins, and the information is mechanically imprinted in area 210, as what is known as an address-o-graph, from an embossed identification card that is created when the patient checks into the hospital. The identification, or address-o-graph, card may include such information as the patient's name, a visit identifier (e.g., by date and/or procedure), a referring physician, the admission date, a billing number, etc., and the card is used for mechanically imprinting this information on every form that is completed during and in connection with the patient's hospital stay.

Filing all the forms in the associated patient charts requires that a filing clerk manually sort and index all forms and physically place each form in the associated patient chart. This process is very time and labor intensive. Moreover, the process is vulnerable to filing mistakes due to errors in reading the identification information imprinted on the form or simple human error in mistakenly placing a form in the wrong patient chart. Furthermore, because blank forms are simply obtained from a forms bin, with no record having been created of the initiation of the form, there is no way to track the forms. If a form is lost or misfiled, the absence of the form may not be readily apparent to the filing clerk or other hospital staff member reviewing the patient chart. This can be especially problematic for forms that comprise multiple pages, all of which are not prepared on the same day. For example, in many hospitals, nurses fill out progress notes during a patient's visit to record the status and progress of the patient as well as other information related to the patient's treatment and condition. As one progress note is completed, a subsequent note is obtained from a blank forms bin and appended to the previously prepared note(s). The preparation of the subsequent progress notes is not recorded and the notes may not be sequentially numbered. For patient visits of significant duration, the progress notes may comprise several sheets of forms. When it is time to file the progress notes into the associated patient chart, there is no way for the filing clerk to know how many progress notes were prepared or in what sequential order they should be filed. Thus, if the progress notes are filed out of order, or one or more sheets of the progress notes is lost or misfiled, such an error or omission can often go undetected.

Subsequent review of the patient chart for follow-up cases or for investigating complications, requires that the patient chart be requested, located, and physically retrieved, which is also labor intensive as well as time consuming. Furthermore, unless duplicate charts are kept in the hospital, which would further exacerbate storage space burdens, if one physician, staff member, or administrator is reviewing a patient's chart, another physician, staff member, or administrator can not simultaneously review the chart.

Thus, a significant need exists for a system and method which reduces the labor requirements of filing and retrieving documentation and improves the accuracy of filing and indexing multiple documents.

SUMMARY OF THE INVENTION

According to one aspect of the invention, a computer system manages the storage of multiple groups of documents. Each group of documents is associated with a characteristic identifying parameter and is comprised of a variety of different types of documents. The system includes a document output device, a document scanning device, memory, and a computer processor. The document output device, for example a printer, creates the different types of documents and forms a machine-readable graphic code on each document. The graphic code has embedded therein document-identifying information including the type of document and the characteristic identifying parameter with which the document will be associated. The document scanning device is constructed and arranged to scan documents created by the document output device and read the machine-readable graphic code and to create a digital data record of each document scanned. The digital data records of the scanned documents are stored in the memory. The computer processor processes the digital data record of each scanned document to identify the type of document and the characteristic identifying parameter of each digital data record and electronically stores each digital data record in a portion of the memory corresponding to the associated characteristic identifying parameter.

According to another aspect of the invention, the machine-readable graphic code is a bar code.

According to another aspect of the invention, a computer-implemented method is provided for storing and indexing a group of documents. Each group of documents is associated with a characteristic identifying parameter and comprises a variety of different types of documents. Each document is generated with a unique graphic code having embedded therein document-identifying information including the type of document and the characteristic identifying parameter with which the document will be associated. A digital data record of each of the documents is created and the unique graphic code of each document is read to identify the type of document and the characteristic identifying parameter with which the document is associated. The digital data records of the documents are indexed according to each document's associated characteristic identifying parameter and are electronically stored in a memory location corresponding to its associated characteristic identifying parameter.

According to another aspect of the invention, a record is made of each document created, and the document-identifying information embedded in each unique graphic code of each digital data record is compared with the document-identifying information of the recorded documents to determine whether or not a digital data record is created for each document created.

According to another aspect of the invention, a computer system for managing the storage of medical forms is provided. Each form is associated with one medical patient of a group of medical patients. The computer system includes a document output device, a document scanning device, memory, and a computer processor. The document output device, for example a printer, creates each of the medical forms and places on each form created a machine-readable graphic code having embedded therein form-identifying information including the type of form and the name of the medical patient with which the form will be associated. The document scanning device is constructed and arranged to scan forms created by the document output device and read the machine-readable graphic code and to create a digital data record of each form scanned. The digital data records of the scanned forms are stored in the memory. The computer processor processes the digital data record of each scanned form to identify the type of form and the medical patient with which each digital data record is associated and electronically stores each digital data record in a portion of the memory corresponding to the associated medical patient.

Other objects, features, and characteristics of the present invention, including the methods of operation and the function and interrelation of the steps and components, will become more apparent upon consideration of the following description and the appended claims, with reference to the accompanying drawings, all of which form a part of this disclosure, and wherein like reference numerals designate corresponding features in the various figures.

DESCRIPTION OF THE DRAWINGS

FIG. 3 shows a typical hospital form with document identifying information provided in a presently used, non-machine-readable format;

FIG. 4 shows how a machine-readable document-identifying graphic code can be incorporated onto a typical hospital form when the form is created for subsequent storing, indexing, and tracking of the form;

DETAILED DESCRIPTION OF THE PREFERRED EMBODIMENT

The present invention will now be described with reference to the accompanying figures. According to the invention, documents of which an electronic record is to be made, for example by scanning, are created, pre-ordered, and provided with a machine-readable graphic code that uniquely identifies the document. When an electronic record of the document is subsequently created, the electronic record includes the document-identifying information derived from the machine-readable graphic code, and the document-identifying information is used to sort the electronic records according to characteristic identifying parameters with which the various groups of documents are associated. The characteristic identifying parameter is part of the document-identifying information embedded in the machine-readable graphic code. The electronic document records are then electronically indexed and stored in a memory area (e.g., a directory or subdirectory) corresponding to a particular characteristic identifying parameter.

The characteristic identifying parameter is some type of unifying parameter with which all documents of a particular group of documents are associated. The characteristic identifying parameter may be, for example, a person, an object, a date, an event, a transaction, or some combination of two or more of these items. In the exemplary application of the present invention described in the Background of the Invention above and in more detail below, for hospital records, the characteristic identifying parameter would be the patient name and the patient visit (i.e., a person and an event). All documents created in connection with a patient's particular visit (e.g., John Doe's hospital stay for gall bladder surgery) will be stored in a particular electronic file corresponding to the patient and visit.

The present invention is particularly applicable to the management, (creating, storing, indexing, tracking, retrieving, etc.) of forms, that is, printed or typed documents with blank spaces for insertion of requested or required information, e.g., manually by handwriting and/or with a typewriter. The invention can also be used in conjunction with systems for creating, tracking, and storing documents that are created entirely electronically, such as electronic forms for which required or requested information is inserted electronically, documents that are transcribed from dictation, or electronically recorded data. Thus, the documents stored in a particular characteristic identifying parameter memory area may comprise a combination of scanned, manually-completed, pre-printed forms and electronically created and completed documents.

Figure 1A:
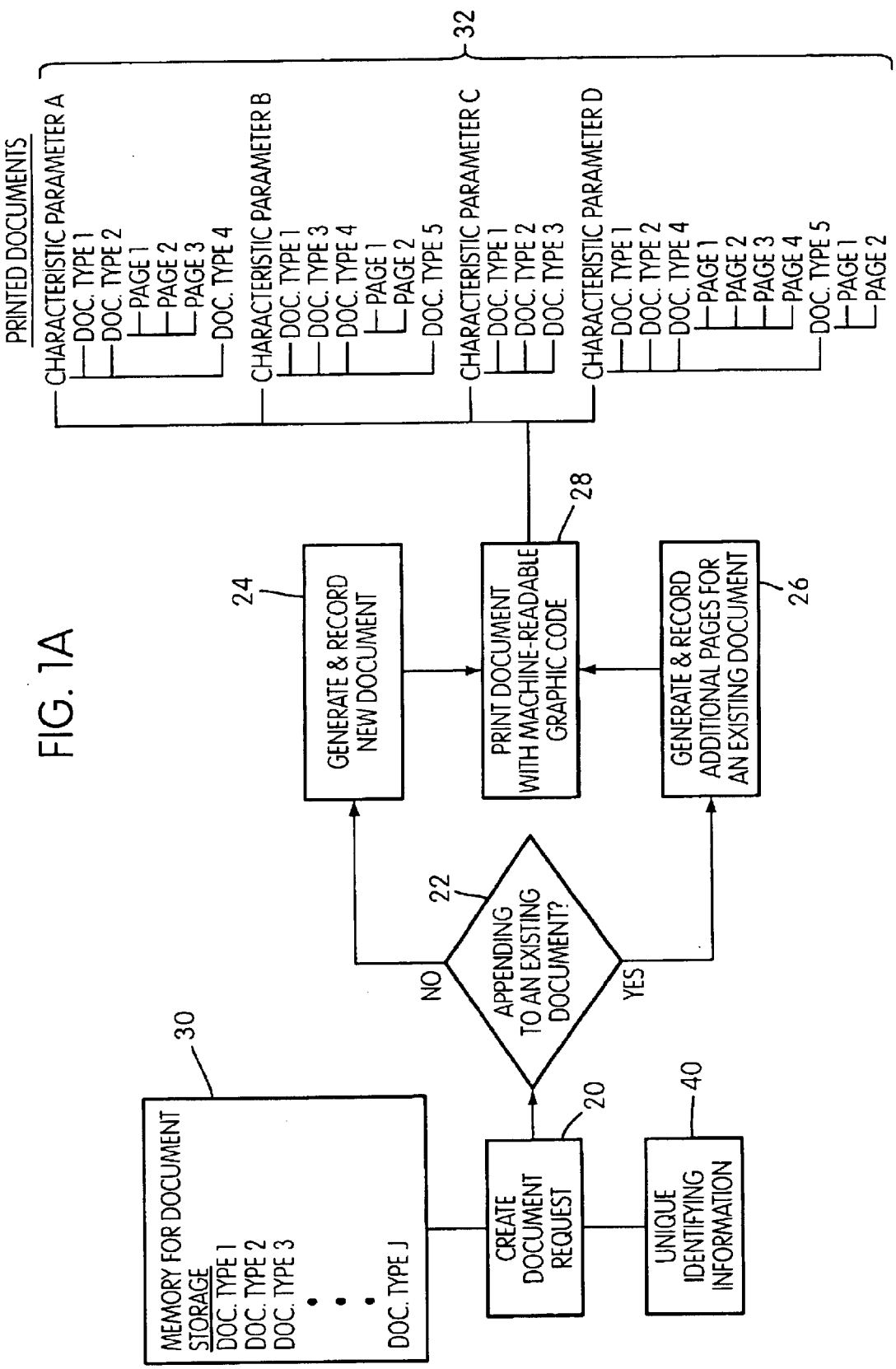
FIG. 1A is a flow chart illustrating a first part of the method of creating, storing, and tracking documents according to the present invention.
Figure 1B:
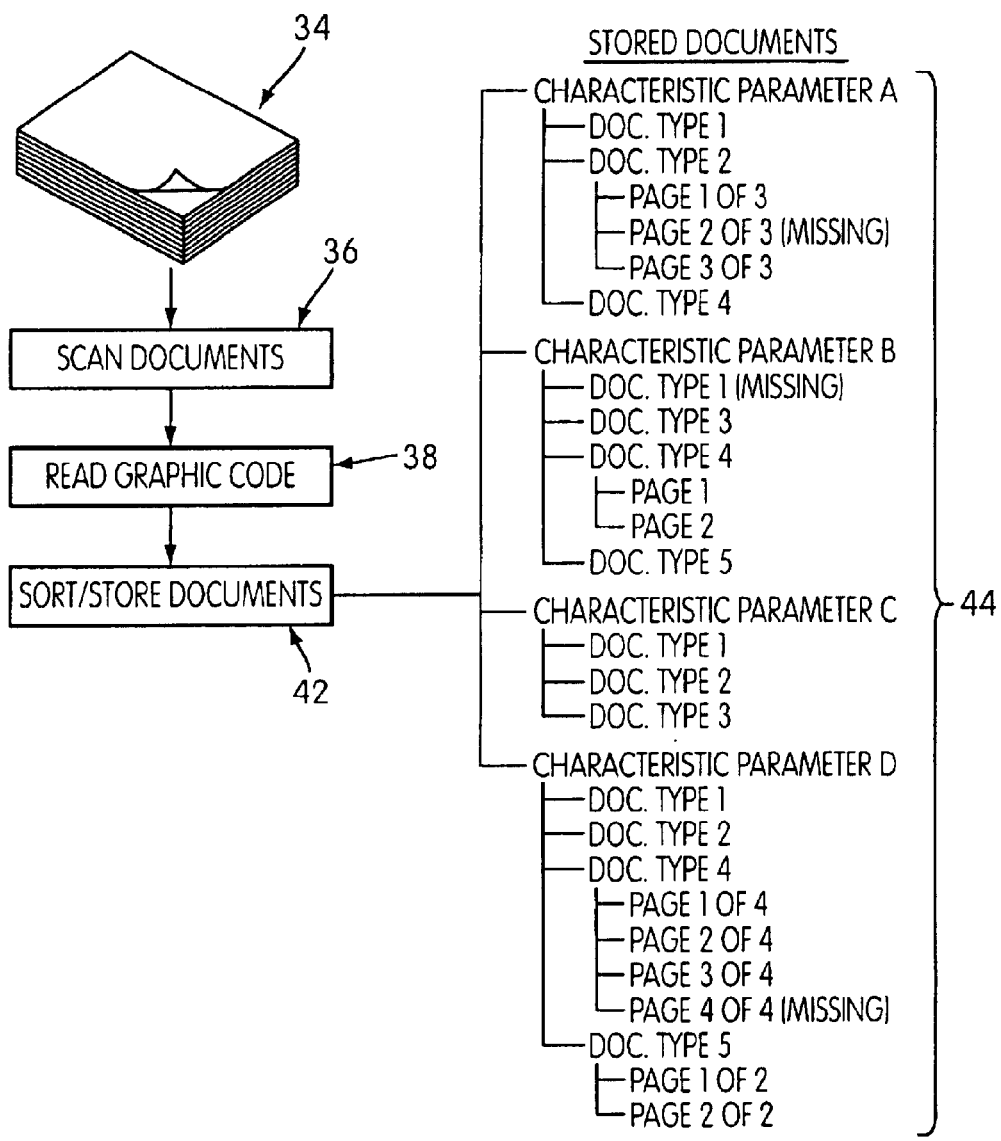
FIG. 1B is a flow chart illustrating a second part of the method of creating, storing, and tracking documents according to the present invention.

The method of the present invention will be described with reference to FIGS. 1A and 1B. FIG. 1A is a flow chart schematically illustrating the steps of the document generation procedure of the method, and FIG. 1B is a flow chart schematically illustrating the steps of the document scanning (electronic record creation) procedure of the method. The method can be implemented on a computer system, as described in more detail below, controlled by appropriately programed software stored on a computer-readable medium.

Referring to FIG. 1A, when a document is created in step 20, the type of document must be specified and unique document-identifying information, including at least the characteristic identifying parameter, must be provided. The type of document is specified from a database 30 of possible document types, [i.e., document type 1-document type j]. The database 30 may be a collection of the different forms employed by a user of the method of which one or more forms are needed at a particular instance for which the documents are being created. Unique identifying information is supplied, as graphically represented at 40. The unique identifying information may contain information that is supplied and input at the time the document creation request is made, or it may be provided from a pre-existing database of unique identifying information. Such information may be added to a database the first time documents to which the identifying information corresponds are created, and thereafter the information may be stored for future access when subsequent documents to which the identifying information applies are created. The unique identifying information, as well as a type-of-document identifier, will be embedded in a machine-readable graphic code, for example, a bar code, that will be placed on the document created.

In step 22, it is determined whether the document requested will be a new, previously non-existing document, or an additional page or pages to be appended onto an existing, previously-created document. If the document to be created constitutes additional pages that are to be appended to a pre-existing document, the graphic code will also have embedded therein information identifying which pages are being generated (e.g., page 2, 3, and 4) of a previously generated document.

The document, whether new (step 24) or appending pages (step 26), is generated, and the creation of the document is recorded for future comparison when digital date records of the documents are subsequently created. The generated document (step 28) will include a machine-readable graphic code. At reference number 32 are represented a number of documents recorded and generated in accordance with the present invention, as well as their organization. Associated with characteristic identifying parameter A, "A" representing, for example, a particular person, object, event, and/or transaction, document types 1, 2, and 4 have been generated, document 2 consisting of three total pages. Note that, depending on specific need, not all documents available in the document memory database 30 will be required for each characteristic identifying parameter. In the illustrated example, document type 3 and document types 5-j of database 30 are not required for characteristic identifying parameter A. Associated with characteristic identifying parameter B, document types 1, 3, 4, and 5 have been generated and recorded, document type 4 consisting of 2 pages. Associated with characteristic identifying parameter C, document types 1, 2, and 3 have been generated and recorded. And associated with characteristic identifying parameter D, document types 1, 2, 4, and 5 have been generated and recorded, document type 4 consisting of four pages and document type 5 consisting of 2 pages.

In the scanning process, (i.e., the process of creating electronic digital data records of the documents) schematically represented in FIG. 1B, the scanning clerk will prepare a stack of documents 34 to be scanned. The documents are placed on and scanned by a scanner at step 36 during which time an electronic digital data record of each document is created and the machine-readable graphic code is read, at step 38, to identify the document. The electronic records are automatically electronically indexed and stored in an appropriate memory location in step 42 based on the identifying information provided in the graphic code.

The stored electronic records and their organization are represented at 44. Under characteristic parameter A, complete electronic digital data records have been created for document types 1 and 4, but in the illustrated example, only pages 1 and 3 of the 3-page document type 2 have been scanned. During the indexing and storing process, the electronic document records 44 are compared to the created documents record 32 (FIG. 1A) to determine whether or not all documents created are subsequently scanned. In the example illustrated in FIG. 1B, a message would be generated notifying the scanning clerk that page 2 of 3 for document type 2 for characteristic identifying parameter A is missing. The clerk could then determine the status of page 2 which may have simply been misplaced, in which case, upon its being located, it can be scanned in to complete this electronic document record for characteristic identifying parameter A, or page 2 may have been intentionally discarded, in which case the electronic records can be adjusted accordingly.

Referring to the electronic document record 44 of the example illustrated in FIG. 1B, under characteristic identifying parameter B, electronic records have been created for document types 3, 4 (both pages), and 5, but no electronic record was created for document type 1. Thus, a message would be generated notifying the clerk that document type 1 for characteristic identifying parameter B is missing.

For characteristic identifying parameter C, electronic records for document types 1, 2, and 3 are created; no documents or pages are missing. For characteristic identifying parameter D, electronic records for documents 1, 2, and 5 (both pages) were created, but no electronic record for page 4 of document type 4 was created. Thus, a message would be generated notifying the clerk that page 4 of 4 of the document type 4 for characteristic identifying parameter D is missing.

Because the documents are indexed based on the identifying information embedded in the machine-readable graphic code, there is no requirement that the stack 34 of documents be pre-sorted. Various document types and characteristic identifying parameters can be commingled; the graphic code of each document provides the information needed to insure that each electronic document record is stored in the proper memory location and that the electronic records 44 can be compared to the created document records 32 to insure that all documents that are created are subsequently scanned and stored or otherwise accounted for. Thus, the electronic data records are complete and accurately indexed, so that they can be readily located and viewed when desired.

To prepare a stack of documents to be scanned, the clerk need only quickly go through the stack and remove any non-scannable documents (i.e., forms or other documents not originally created in accordance with the invention and thus not including a machine-readable graphic code) and remove staples and paper clips from the stack. Preferably both one and two sided documents can be scanned and the graphic code can be read even if the document is upside-down and regardless of whether the graphic code faces up or down.

Figure 2:
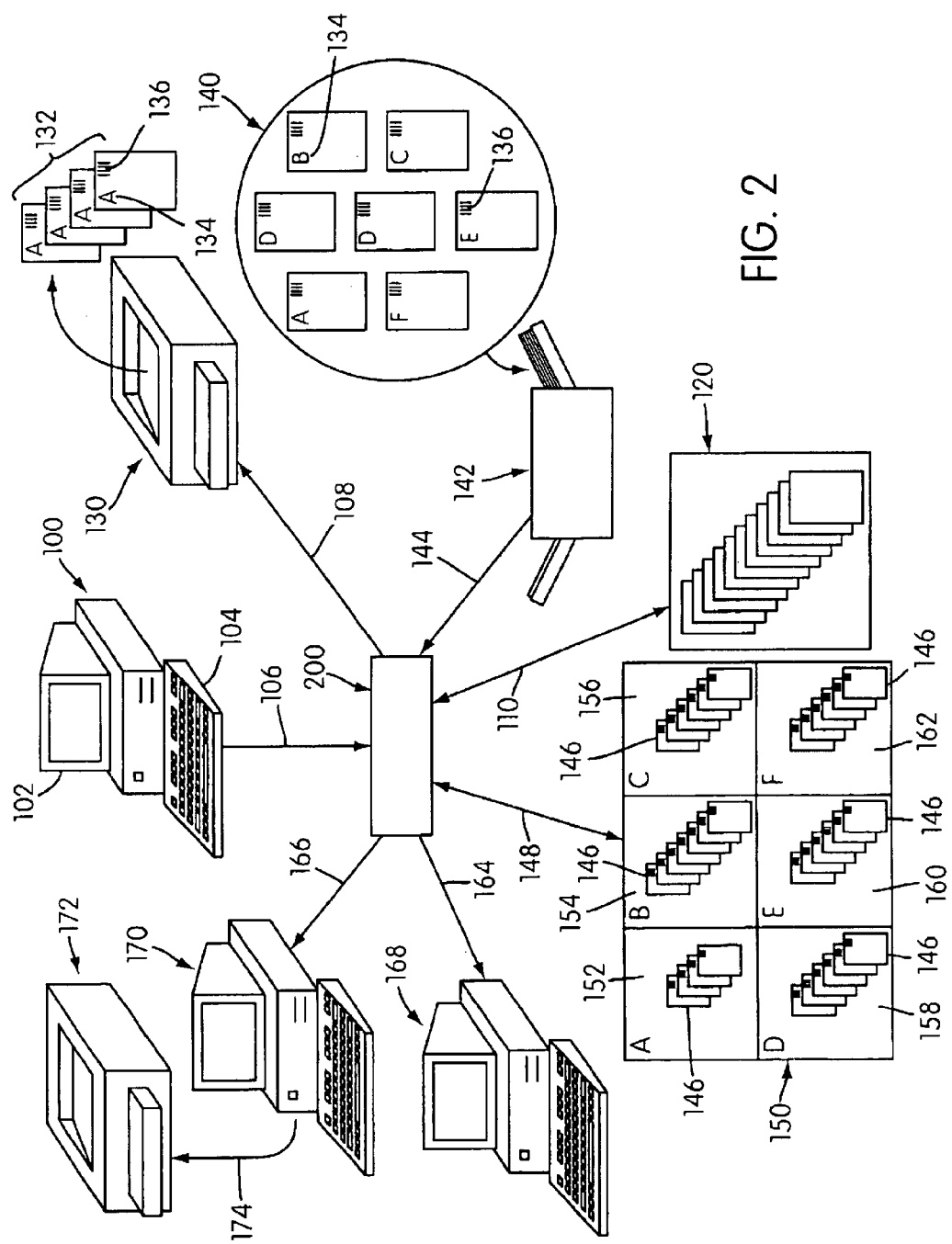
FIG. 2 is a schematic representation of a computer-based system for creating, storing, and tracking document in accordance with the present invention.

A computer system for implementing the present invention is schematically represented in FIG. 2. The system may comprise one or more computer machines (processors), printers, scanners, and memory storage devices connected to a server. The system is preferably a 32-bit Microsoft Windows®-based system using standard PC and networking technology. The components of the system may communicate with one another over a local area network (LAN) or a wide area network (WAN). In addition, one or more of the computer machines may be configured to communicate with the server over an internet link (e.g., the worldwide web) or an intranet. The system setup shown in FIG. 2 is intended to schematically illustrate the various components that would make up a system for implementing the present invention and is not intended to be a limiting illustration of the system.

Identifying data is entered at computer machine 100 which would typically include a monitor 102 and a keyboard 104. As an alternative to, or in addition to, the keyboard 104, computer 100 may include and accommodate other means of data input, such as a mouse, a touch sensitive screen, or voice recognition. Document generation requests can be entered at the computer 100 (known as the host system), and document-identifying information, including the characteristic identifying parameter, can also be entered at the computer 100.

Computer 100 communicates, via communication links 106 and 110 and server 200, with memory area 120 at which is stored a database containing the various document types that have been selected by the user of the invention to be the types of documents for which electronic records will be created. The record storage and retrieval system preferable employs Microsoft SQL databases. Documents (e.g., forms) may be placed in memory area 120 for access by a computer machine 100 in any known manner, such as by scanning pre-existing documents and saving the electronic digital record crated thereby to area 120, or by saving to memory area 120 documents that are electronically generated, e.g., using wordprocessing software. As mentioned above, it may be desirable to save the document-identifying information, including the characteristic identifying parameter, that is entered at computer 100 for future access and use when creating subsequent documents to be associated with the same characteristic identifying parameter, and memory storage space is preferably provided to store such data. The dedicated storage space is not explicitly shown in FIG. 2, but such data could be stored, for example, on the hard drive of computer 100 or in some other storage location.

Using computer 100, the desired document type(s) of those document types available in memory area 120 are selected and the characteristic identifying parameter information is specified (or selected from a database of characteristic identifying parameter data). This information is communicated, via the server 200 and communication links 106, 108, and 110, to a printer 130 which prints the requested documents 132 with a machine-readable graphic code 136, for example a bar code, and, in a preferred embodiment, an alphanumeric, human readable, identifying insignia 134.

When the documents are ready to be scanned to create electronic data records of all the documents (e.g., when the forms have been filled out and completed) a stack of forms, schematically represented at 140, is placed on a scanner 142. Note that the stack of documents 140 includes commingled, unordered documents associated with the characteristic identifying parameters A, B, C, D, E, and F. It is preferred that a high-speed scanner capable of accommodating stacks of documents be used. Suitable scanners include Kodak and Hewlet Packard scanners with Kofax® image products. It is possible, though not preferred, to scan in documents one-at-a-time on a flat-bed scanner.

Scanner 142 communicates, via server 200 and communication links 144 and 106 with computer 100 and via communication link 148 with memory area 150. The processor of the host system is programmed to index the electronic document data records 146 according to the document-identifying information embedded in the respective unique graphic codes 136 and store the electronic data records 146 in storage locations 152, 154, 156, 158, 160, and 162 of storage area 150 corresponding to characteristic identifying parameters A, B, C, D, E, and F, respectively.

The indexed digital data records 146 can subsequently be accessed by other computers 168, 170, as well as computer 100, which communicate with the server 200 via communication links 164, 166, and 106, respectively. The storage and retrieval system preferably employs the OTG DiskXtender™ automated storage retrieval system. Once the electronic document data records are accessed, any selected document can be viewed on a computer monitor, printed on a printer 172, with which computer 170 communicates via communication link 174, and/or downloaded to a portable device, such as a personal digital assistant. The computer system can also be configured such that document creation requests and/or characteristic identifying parameter data input can be performed at more than one computer connected to the system, such as computers 168 and/or 170, as well as computer 100.

A particularly advantageous application of the present invention is in the storing, indexing, tracking, and retrieving of patient records at a hospital.

Figure 4:
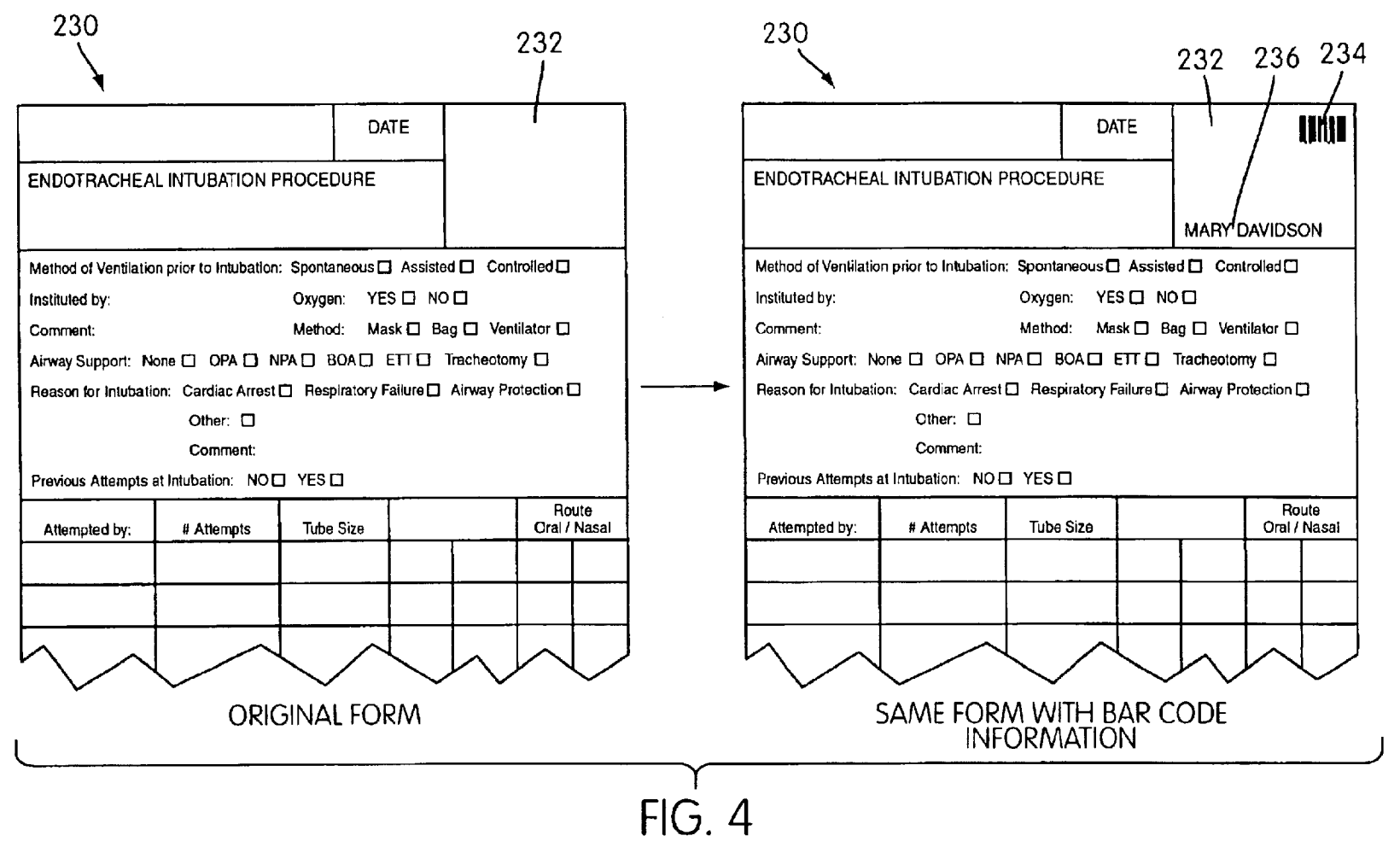

FIG. 4 illustrates how a typical hospital form, in the example shown, an Endotracheal Intubation Procedure form 230, can be modified in accordance with the present invention. In the blank space 232 at the upper right-hand corner of the form, where the address-o-graph would previously have been imprinted (see FIG. 3), a bar code 234 and the patient's name 236 are printed when the form 230 is generated. Thus, a particular advantage of the system and method of the present invention is that it can be implemented essentially without changing the forms used by the hospital prior to implementation of the invention. Accordingly, procedures and protocols for completing forms do not need to be redefined by hospital administrators nor re-learned by hospital staff. The only difference in the procedure is that rather than going to a blank forms bin every time a new form is needed, the hospital staff member would generate the form from a computer, selecting the form desired and designating the patient for whom the form is needed. As described above, once such a form is generated, whether it is a new form or appending pages for a pre-existing form, an electronic record of that form is created so that the form can be tracked.

Figure 5:
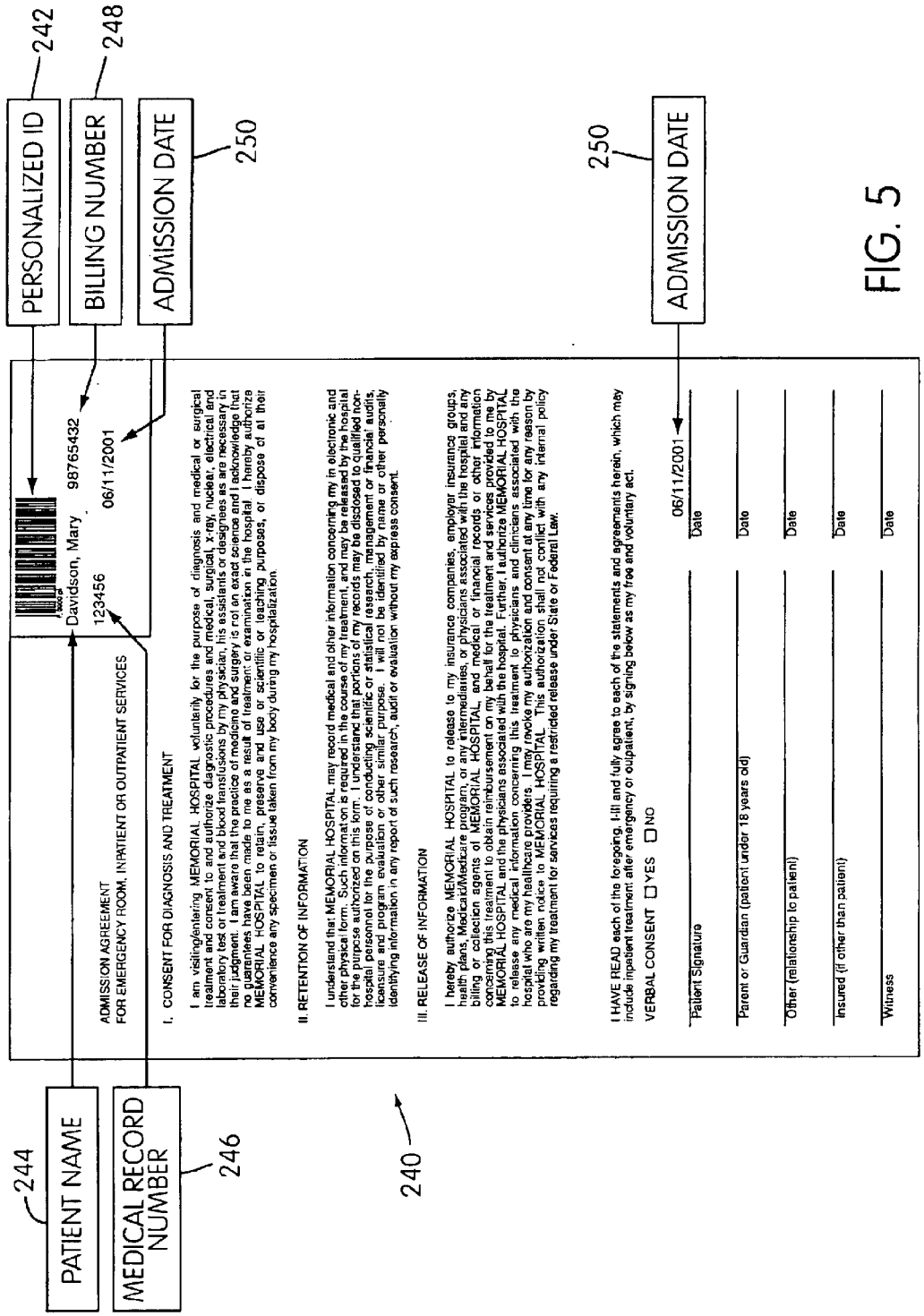
FIG. 5 shows a typical hospital form with document-identifying insignia, including a machine-readable graphic code, printed on the form when the form is created.

FIG. 5 shows a preferred format for a form 240 with pre-printed information in accordance with the present invention. In the upper right-hand corner, the bar code personalized ID 242, the patient name 244, the medical record number 246, the billing number 248, and the admission date 250 are printed. In the case of the admission agreement form shown which, in most instances would be signed by the patient on the date of admission, the admission date may also be pre-printed adjacent the patient signature line. Other forms that would in the normal course of business be expected to be signed on the date they are generated, e.g., a release form, can be generated with the current date pre-printed adjacent the appropriate signature line(s).

Forms can be electronically placed into the forms database in one of two ways. Existing blank forms can be scanned in or forms that already exist in electronic format can be imported. A document layout definition (DLD) is created for the existing forms, now stored electronically in the forms database, and is required for each document that will be scanned. The DLD includes information regarding the configuration and format of the document, such as whether the document is single or double-sided, where important information (such as the patient name or medical record number) is located on the form, the size and location of the bar code, and type of information that will be embedded in the bar code, such as document type and patient and visit information. The DLD can also specify the area of the document the scanner will capture. This makes it possible to reduce the size of electronic files for documents which do not require the entire 8.5×11 inch area the scanner typically captures. In the DLD, it may also be desirable to specify double-sided scanning of the first page of a multi-page document and to discard the back sides of the remaining pages of the document if each page has instructions for completing the form printed on the back. Thus, when such multi-page, two-sided documents are scanned, only the back side of the first page is scanned, thereby saving only one copy of the instructions and keeping the size of electronic files to a minimum.

Medical forms can be scanned into a patient file database in batches. Stacks of forms, which need not be sorted and in which different patients' forms can be commingled, are placed on a scanner. Using the document-identifying information (i.e., patient name/visit and document type) provided by the bar code, the electronic records of the forms are automatically saved under the correct patient name and the system ensures that all documents that are generated are subsequently scanned.

Future viewing of a patient chart, or any part thereof, is easily achieved on any computer machine having access to the records storage server. Thus, for example, a surgeon viewing a particular form of a patient's chart on a computer monitor in the operating room can confer with a colleague viewing the same form on a monitor located in a different part of, or possibly outside of, the hospital.

Figure 6:
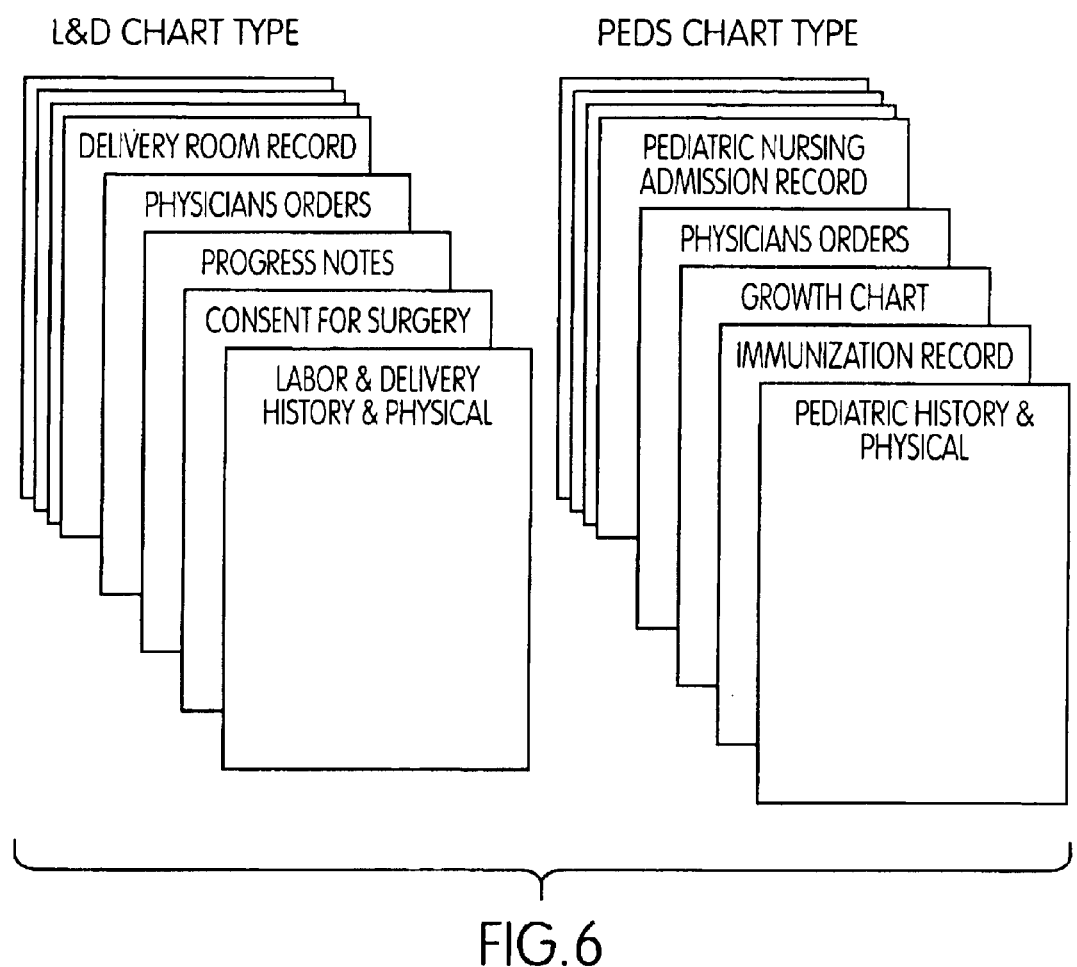
FIG. 6 shows collections of hospital forms specifically tailored to the nature of the patient's visit.

Often, in the course of a hospital stay, there are particular collections of forms that always must be completed, depending on the nature of the patient's visit. For example, for an L & D (labor and delivery) hospital visit, the patient's file would include a Labor and Delivery History and Physical form, a Consent For Surgery form, Progress Notes, Physician's Orders, and a Delivery Room Record. Similarly, for a PEDS (pediatrics) hospital visit, the patient's file would include a Pediatric History and Physical, an Immunization Record, a Growth Chart, Physician's Orders, and a Pediatric Nursing Admission Record. Under the present invention, collections of forms, referred to as chart types, can be defined for a variety of procedures. Labors and delivery and PEDS chart types are schematically shown in FIG. 6. Thus, when a patient checks in, after the admissions clerk has entered all the necessary identification, billing, and insurance information, an applicable chart type can be assigned to the patient, depending on the purpose of the visit, and the appropriate collection of forms, each personalized for that patient, is generated. This saves time by eliminating the need to separately specify and generate each form and prevents the possibility that a necessary form will be forgotten or overlooked and thus, need to be generated later.

While the invention has been described in connection with what are presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

What is claimed is:

1. A computer system for managing the storage of multiple groups of documents, each group of documents being associated with a characteristic identifying parameter and comprising different types of documents, said computer system comprising:

a document output device constructed and arranged to generate the different types of documents and to form on each document a machine-readable graphic code when the document is originally generated, the graphic code relating to document-identifying information including the type of document and the characteristic identifying parameter with which the document will be associated;

a document scanning device constructed and arranged to scan documents generate by said document output device to create a digital data record of each document scanned and to read said machine-readable graphic code;

memory for storing the digital data records of the scanned documents; and a computer processor for processing the digital data record of each scanned document to identify the type of document and the characteristic identifying parameter of each digital data record and to electronically store each digital data record in a portion of said memory corresponding to the associated characteristic identifying parameter.

2. The computer system of claim 1, further comprising a computer machine including a data input device constructed and arranged to permit the electronic input of the characteristic identifying parameter.

3. The computer system of claim 1, wherein said machine-readable graphic code is a bar code.

4. The computer system of claim 1, further comprising a computer machine including a data input device constructed and arranged to permit the electronic input of a document creation request in which the type of document requested is specified and the characteristic identifying parameter is defined for the requested document.

5. The computer system of claim 1, further comprising a second memory for storing a database of different characteristic identifying parameters.

6. The computer system of claim 1, further comprising a computer machine in communication with said memory for accessing selected digital data records and for viewing a scanned document corresponding to the selected digital data records.

7. The computer system of claim 1, wherein said computer processor is constructed and arranged to process a plurality of randomly-ordered digital data records, each digital data record being associated with one of two or more different characteristic identifying parameters, and to automatically group the digital data records according to their associated characteristic identifying parameters for storing the digital data records in the portion of memory corresponding to the associated characteristic identifying parameter.

8. The computer system of claim 1, wherein the document-identifying information of the machine-readable graphic code also includes the page number of multipage documents.

9. The computer system of claim 1, wherein said document-identifying information is embedded in said machine-readable graphic code formed on each document by said document output device.

10. A computer-implemented method for storing and indexing a group of documents, each group of documents being associated with a characteristic identifying parameter and comprising different types of documents, said method comprising:

originally generating each document with a unique graphic code relating to document-identifying information including the type of document and the characteristic identifying parameter with which the document will be associated;

creating a digital data record of each of the documents and reading the unique graphic code of each document to identify the type of document and the characteristic identifying parameter with which the document is associated; and indexing the digital data records of the documents according to each document's associated characteristic identifying parameter and electronically storing each digital data record in a memory location corresponding to its associated characteristic identifying parameter.

11. The computer implemented method of claim 10, further comprising:

recording the document identifying information of each document generated; and comparing the document-identifying information related to each unique graphic code of each digital data record with the recorded document-identifying information to determine whether or not a digital data record is created for each document generated.

12. The computer implemented method of claim 10, wherein said graphic code comprises a bar code.

13. The computer implemented method of claim 10, wherein said characteristic identifying parameter comprises a person, an object, a date, an event, a transaction, or some combination thereof which uniquely identifies the group of documents associated with the characteristic identifying parameter.

14. The computer implemented method of claim 10, further comprising maintaining a database of document types from which a desired document type may be selected during said document generating step.

15. The computer implemented method of claim 10, further comprising maintaining a database of characteristic identifying parameters from which a desired characteristic identifying parameter may be selected during said document generating step.

16. The method of claim 10, further comprising automatically processing a plurality of randomly-ordered digital data records, each digital data record being associated with one of two or more different characteristic identifying parameters, and automatically grouping the digital data records according to their associated characteristic identifying parameters for storing the digital data records in the memory location corresponding to its associated characteristic identifying parameter.

17. The method of claim 10, wherein the document-identifying information is embedded in the unique graphic code on each document generated.

18. A computer system for managing the storage of medical forms, each form being associated with a particular medical patient, said computer system comprising:

a document output device constructed and arranged to generate each of the medical forms and to place on each form a machine-readable graphic code when the form is originally generated, the graphic code relating to form-identifying information including the type of form and the name of the medical patient with which the form will be associated;

a document scanning device constructed and arranged to scan forms generated by said document output device to create a digital data record of each form scanned and to read said machine-readable graphic code;

memory for storing the digital data records of the scanned forms; and a computer processor for processing the digital data record of each scanned form to identify the type of form and the medical patient with which each digital data record is associated and to electronically store each digital data record in a portion of said memory corresponding to the associated medical patient.

19. The computer system of claim 18, further comprising a computer machine including a data input device constructed and arranged to permit the electronic input of the patient name.

20. The computer system of claim 18, wherein said machine-readable graphic code is a bar code.

21. The computer system of claim 18, further comprising a computer machine including a data input device constructed and arranged to permit the electronic input of a form creation request in which the type of form requested is specified and the patient name is defined for the requested form.

22. The computer system of claim 18, further comprising a second memory for storing a database of different patient names.

23. The computer system of claim 18, further comprising a computer machine in communication with said memory for accessing selected digital data records and for viewing a scanned form corresponding to the selected digital data records.

24. The computer system of claim 18, wherein said form-identifying information is embedded in said machine-readable graphic code formed on each medical form by said document output device.

25. A computer readable medium having instructions encoded thereon for causing an electronic computer system to implement a method for storing and indexing a group of documents, each group of documents being associated with a characteristic identifying parameter and comprising different types of documents, said method comprising:

originally generating each document with a unique graphic code having embedded therein relating to document-identifying information including the type of document and the characteristic identifying parameter with which the document will be associated;

creating a digital data record of each of the documents and reading the unique graphic code of each document to identify the type of document and the characteristic identifying parameter with which the document is associated; and indexing the digital data records of the documents according to each document's associated characteristic identifying parameter and electronically storing each digital data record in a memory location corresponding to its associated characteristic identifying parameter.

26. A computer readable medium having instructions encoded thereon for causing an electronic computer system to implement a method for storing and indexing a group of medical forms, each group of forms being associated with a particular medical patient, said method comprising:

originally generating each medical form with a unique graphic code relating to document-identifying information including the type of medical form and the patient name with which the form will be associated;

creating a digital data record of each of the forms and reading the unique graphic code of each form to identify the type of form and the patient name with which the form is associated; and indexing the digital data records of the forms according to each form's associated patient name and electronically storing each digital data record in a memory location corresponding to its associated patient name.

27. The computer readable medium of claim 26 having further instructions encoded thereon for causing the electronic computer system to selectively generate in response to a single form generation request a collection of forms each being associated with a particular patient name, wherein the collection of forms is defined by the purpose of the particular patient's hospitalization.

* * * * *